(12) United States Patent
Syed Muhammad et al.

(10) Patent No.: US 9,028,891 B2
(45) Date of Patent: May 12, 2015

(54) NATURAL COLORANT AND METHODS THEREOF

(75) Inventors: Sharifah Kharidah Syed Muhammad, Selangor (MY); Hossein Amin, Fars (IR); Jamilah Bakar, Selangor (MY)

(73) Assignee: University of Putra Malaysia, Serdang Baharu (MY)

( * ) Notice: Subject to any disclaimer, the term of this patent is extended or adjusted under 35 U.S.C. 154(b) by 991 days.

(21) Appl. No.: 13/012,423

(22) Filed: Jan. 24, 2011

(65) Prior Publication Data

US 2011/0207683 A1    Aug. 25, 2011

Related U.S. Application Data (63) Continuation of application No. PCT/MY2009/000023, filed on Feb. 6, 2009.

(51) Int. Cl.
*A61K 36/33* (2006.01)
*A61K 9/16* (2006.01)
*C09B 61/00* (2006.01)

(52) U.S. Cl.
CPC ............... *A61K 9/1652* (2013.01); *C09B 61/00* (2013.01)

(58) Field of Classification Search
USPC .......................................................... 424/767
IPC ...................................................... A61K 36/33
See application file for complete search history.

(56) References Cited

U.S. PATENT DOCUMENTS 7,208,181 B1 *   4/2007   King et al. .................... 424/725

FOREIGN PATENT DOCUMENTS

| CN | 1631987 | * | 6/2005 |
| CN | 1806675 | * | 7/2006 |
| JP | 2003253147 | * | 9/2003 |
| JP | 2008061537 | * | 3/2008 |

OTHER PUBLICATIONS

Herbach et al. Eur. Food Res. Technol. 2007. vol. 224, pp. 649-658.*
Herbach et al. Food Res. Intl. 2006. vol. 39, pp. 667-677.*
Wybraniec et al. J. Agric. Food Chem. 2002. vol. 50, pp. 6086-6089.*
Stintzing et al. Eur. Food Res. Technol. 2003. vol. 216, pp. 303-311.*
Mobhammer et al. J. PACD. 2006. pp. 1-25.*
Mobhammer et al. Innovative Food Sci. Emerging Technol. 2006. vol. 7, pp. 275-287.*
Stintzing et al. Food Chem. 2002. vol. 77, pp. 101-106.*

* cited by examiner

*Primary Examiner* — Chris R Tate
(74) *Attorney, Agent, or Firm* — Locke Lord LLP; Ralph A. Loren; Limor Gabay (57) ABSTRACT

To provide a material composed mainly of a material derived from dragon fruit having to provide a supplement, a drug, a cosmetic or a food produced by using the material. The invention provides a material derived from dragon fruit, especially, a powder of dragon fruit, and a supplement, a drug, a cosmetic or a food containing the above material as a component.

3 Claims, 5 Drawing Sheets

Fig. 1. Surface plot of betalain retention versus maltodextrin concentration and outlet air temperature. Inlet air temperature: 150°C.

Fig. 2. Surface plot of 'a' value versus outlet air temperature and inlet air temperature. 18% of maltodextrin used.

Fig. 3. Surface plot of moisture content versus maltodextrin concentration and outlet air temperature. Inlet air temperature: 150°C.

Fig. 4. Surface plot of water activity ($a_w$) versus maltodextrin concentration and outlet air temperature. Inlet air temperature: 150°C.

Fig. 5. Surface plot of hygroscopicity versus maltodextrin concentration and outlet air temperature. Inlet air temperature: 150°C.

NATURAL COLORANT AND METHODS THEREOF

RELATED APPLICATIONS

This application is a continuation of PCT/MY2009/000023 filed on Feb. 6, 2009, the entirety of which is herein incorporated by reference

FIELD OF INVENTION

The invention relates to a water dispersible composition, preferably a natural colorant powder from fruit, its method of preparation as well as its use as primary composition in the preparation of various food products, food supplements, pet food products, pet food supplements or neutraceutical or cosmetic or pharmaceutical preparations.

BACKGROUND OF INVENTION

Currently, food colours are manufactured from organic/inorganic synthetic sources and are considered to be potentially harmful. Pigments and bioactive compounds extracted from fruits or plant materials are widely used in the food industry as functional ingredients. Many other bioactive ingredients are also well perceived by consumers for their beneficial properties, but their application in e.g. food products is either difficult or provides poor bioavailability. In addition to that, current extraction techniques afford the desired ingredients in very low yield and lead frequently to some deterioration of the genuine properties of the extracted ingredients. Betalains, a group of naturally occurring pigments, include the betacyanins which are red-violet and the betaxanthins which are yellow. Betalains have been detected only in red-violet, orange and yellow pigmented botanical species belonging to related families of the order caryophyllales. Of the numerous natural sources of the betalains, red beet and prickly pear are the only edibles containing high concentrations of these pigments. The betacyanins are derived from two aglycons, betanin and iso-betanidin. Betanin is a betanidin 5-O-β glucoside. Betanidin contains an ortho-diphenol group, which is suspected to be a very good electron donor or hydrogen donor, working as an active antioxidant. In addition to their antioxidative effects, betanin and betanidin are cationized molecules which may increase their protective effects on cells and organelles against oxidation. Cell and organelle membranes are negatively charged and anionic sites on the cell surface have been shown to exhibit strong affinity for cationic agents.

Dragon fruit which is known as pitaya, pitahaya, pitajaya, or pitaya roja belongs to the *Hylocereus* sp. from the Cactaceae family (Luders and McMahon, 2006). The usage of purple-flesh (red-violet) dragon fruit (*Hylocereus polyrhizus*) as a good source of betalains has been highlighted by several authors (Stintzing et al., 2002; Wybraniec et al., 2001). The colour of betalain is close to that of anthocyanins but is three times stronger (Stinzing and Carle, 2007). Betalains are also more water soluble than the anthocyanins (Stintzing et al., 2006). They make a good choice for colouring of low-acid foods because, compared to anthocyanins, they maintain their colour in the pH range of 3 to 7 (Stintzing and Carle, 2004).

Dragon fruit can be powdered to have a longer shelf life and therefore could be easily and readily available and served as a good source of betalain rich functional food ingredient for addition into food products as natural color or having instant properties. In addition, the powder form can be very stable due to its low water activity and therefore low biochemical reactions. Spray drying of fruits which contain high sugar and organic acid contents is difficult. These compositions have a sticky behavior during spray drying. Stickiness depends on the properties of the materials and also involved the inlet variables applied in the spray drying process. Deposition is another problem that arises from the stickiness and the design of the drier. If the size of the chamber is large enough, there will not be deposition problem but because of economic factors, the size of the chamber would be limited to a suitable size. Therefore, the stickiness and deposition should be solved by other methods (Truong et al., 2005). The sticky behavior of sugar and acid rich materials is related to the low molecular weight of sugars (fructose, glucose and sucrose) and organic acids (citric, malic and tartaric acid) whereby 90% of solids in fruits are of these compounds (Bhandari et al., 1997). Some additives such as maltodextrin have been used to reduce the stickiness and deposition in spray drying of foods such as blackcurrant (Bhandari et al., 1993), honey (Bhandari et al., 1997), tamarind (Truong, 1994), watermelon (Quek et al., 2007), and pineapple (Abadio et al., 2004). Different types of maltodextrin with dextrose equivalent (DE) ranging from 5 up to 40 are available commercially. The higher the DE of a maltodextrin, the lower is the chain length of its glucose polymer. Maltodextrins are the most common of additives used for drying of fruit powders and usually, the fractions of these carriers are 40 to 60% but higher amounts can also be used (Masters, 1994). There is a complex interaction between spray drier apparatus, process, and product parameters (solid content, viscosity, and temperature) which affect the quality of the powder. The most effective factors in a spray drying process are feed flow rate, inlet and outlet air temperatures, atomizer speed, feed concentration, feed temperature, and inlet air flow rate (Chegini, & Ghobadian, 2005). The aim of this study is to investigate the relationship between inlet air temperature, outlet air temperature, and maltodextrin concentration as important factors in spray drying of dragon fruit and to evaluate their effects on the betalain content and physical properties of the powder produced.

Fruits are usually rich in reducing sugars, making the drying of their juice and handling of their powder very difficult. There may also be lost of some colour in the fruit powder or low stability and short shelf life of the powder during storage. A large number of extraction and concentration techniques are already known. The techniques, however, may be costly. In addition, there may be some technical problems at the time of applying the fruit powder as natural colour. It is thus an object of the present invention to address the above problems by providing a simple and cheap method for producing a natural colorant (preferably known also as betalain) from a fruit with improved stability, miscibility, dispersibility in aqueous systems and, also, with enhanced bioavailability as compared to similar extracts from the prior art. This invention relates to natural colorants as a bioactive ingredient preferably used in foodstuffs, neutraceuticals, pharmaceuticals and cosmetics. The natural colorant is in a form of powder and which the powder is suitable to be used as an additive agent, in foodstuffs which include dairy and ice-cream products, jellies, snacks, confectionaries, alcoholic and non-alcoholic beverages, pharmaceuticals and cosmetics which contain betalain especially. Moreover, the present invention relates the natural colorants containing betalains obtained from fruits, preferably dragon fruit (*Hylocereus polyrhizus*), useful for prevention and treatment of disorders and diseases that are due to oxidative stress, especially vascular diseases or the compositions may be pharmaceutical compositions containing, as an active ingredient, betacyanins that are produced from dragon fruit (*Hylocereus polyrhizus*). The advantage of the present invention also relates to a cost effective method and manufacturing method of foodstuff or pharmaceutical or cosmetic products containing betalain as a natural colorant obtained from dragon fruit (*Hylocereus polyrhizus*

SUMMARY OF INVENTION

The present invention discloses a process for manufacturing natural colorant obtained from a fruit, characteristically from *Hylocereus polyrhizus* or red dragon fruit. The process in this present invention includes; obtaining red dragon fruits, removing skin and seeds from the fruits, obtaining a liquid solution from the skin removal, further, adding an anti-sticking or encapsulating material (preferably, the anti-sticking or encapsulating material is maltodextrin or resistant maltodextrin) into the liquid solution, then, mixing the anti-sticking or encapsulating material and liquid solution to form a homogenized mixture. Later, storing the mixture for at least two hours and then, adding the mixture from into drying apparatus (preferably include a cabinet drier, drum drier, freeze drier or spray drier to obtain a dry powder. Accordingly, the natural colorant is a bioactive ingredient, wherein the natural colorant includes betalains. Indeed, the preferred amount of maltodextrin or resistant maltodextrin having a working amount between 5% and 30% (w/w juice).

The process of spray drying further includes; having a working inlet air temperature between 130° C. and 190° C. and having a working outlet air temperature between 50° C. and 100° C. Yet, the embodiment of the present invention relates to a natural colorant comprising betalains is prepared by the above mention processes and preferably the colorant having the means to be prepared into a powder. In addition, the present invention also relates to the use of the natural colorant comprising betalains obtained from dragon fruit/s for the manufacture of a food ingredient, food product or foodstuff, pharmaceutical or neutraceutical composition, cosmetic or topical preparation. Preferably, the cosmetics include cream, lotion, eye cream, ointment or gel, sun-screen, oral administration, face mask, blusher, eye shadow, lipstick. The pharmaceutical compositions include tablets, syrups and capsules and the food products include beverages, dairy products, ice-cream, sherbets, ice preparations, confectionaries, snacks, candies, fruit toffees, fruity dry mixes, jellies, fruit fillings, toppings, chocolates, seasonings. Indeed, the natural colorant is use in any application in food formulation/s as an ingredient, additive or for any functional properties, further to that, the natural colorant is used in the neutraceuticals including antioxidant and dietary fibre preparations.

DETAILED DESCRIPTION OF INVENTION

The present invention relates to a method for producing high betalain dragon fruit powder, which is a natural colour and has biological activity or health impact when orally ingested or applied in cosmetic, in a pilot plant scale. Wherein the dragon fruit powder has good physical properties that is obtained by using 22% of maltodextrin DE8-12 (w/w juice), outlet air temperature of 75° C., and inlet air temperature of 150° C. It is observed that the increasing of maltodextrin prevents stickiness, increased betalain retention, decreased moisture content and water activity, and decreases the hygroscopicity of the powder.

BEST MODE TO CARRY OUT THE INVENTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. It must be noted that as used herein and in the appended claims, the singular forms "a," "an," and "the" include plural referents unless the context clearly dictates otherwise.

MATERIALS AND METHODS

Materials

Red dragon fruits (*Hylocereus polyrhizus*) were purchased from a plantation in Melaka, Malaysia. All chemicals were bought from Merck. Maltodextrin DE8-12 was a gift from San Soon Seng Food Industries, Selangor, Malaysia.

Methods a) Preparation of Juice

Fresh dragon fruits were peeled manually. The seeds were separated and removed by straining the fruit pulp through the sieve of a finisher (Bonina, ITABUNA, BA). The juice was stored at −20° C. prior to spray drying.

b) Preparation of Sample and Spray Drying

Frozen juice was thawed and maltodextrin DE8-12 was then added to the juice.

The mixture was homogenized for 10 min at 9500 rpm using a T25 basic lab homogenizer (IKA-WERKE, Germany) and stored for 2 hours prior to spray drying.

Figure 1:
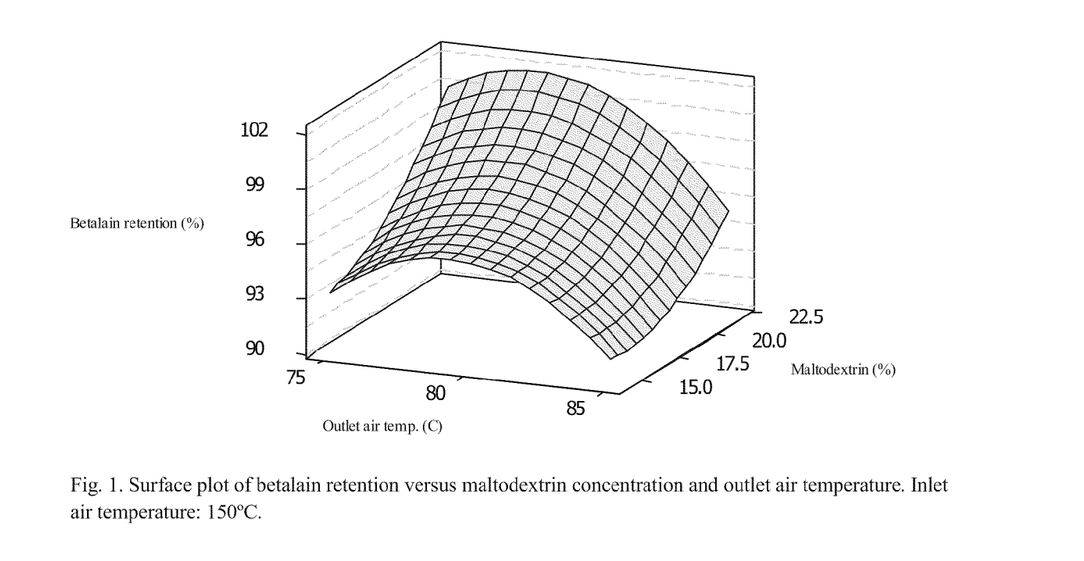
FIG. 1 shows a surface plot of betalain retention versus maltodextrin concentration and outlet air temperature.

A pilot spray drier (Model Niro A/S, GEA, Germany) was used for the spray drying process. Spray drying was carried out with 900 m$^3$/min of air flow rate, rotary atomizer type with speed of 15000 rpm, and feed temperature of 40° C. These conditions were chosen after conducting initial trial runs. Inlet air temperature limits of 150-170° C., outlet air temperature limits of 75-85° C., and 14 to 22% (w/w) maltodextrin DE8-12 added to the juice were chosen as independent variables. The dependent variables were betalain content, color, moisture content, water activity, hygroscopicity, and solubility of the dragon fruit powder produced.

through the cuvette. For quantification of betacyanins, the molecular weight (MW) and molar extinction coefficient ($\epsilon$) of betanin (MW=550 g/mol; $\epsilon$=60,000 L/mol cm; $\lambda$=538 nm), constituting the major betalains in dragon fruit juice, were employed. The determinations were performed in triplicates. FIG. 1 shows the surface plot of betalain retention versus variables. The full quadratic for betalain retention was illustrated in Table 1. Based on the regression coefficients and statistical analysis at p <0.05, there was moderate relationship between independent variables and betalain retention. It means that betalain was stable when spray dried at 150-170° C., although as shown in FIG. 1, lower temperatures and higher maltodextrin concentrations lead to higher amount of betalain retention.

TABLE 1

Regression coefficients, $R^2$, and probability, p values for five responses for spray drying of dragon fruit juice

| Coefficients | Betalain retention | Color (a) | Color (L) | Moisture content | Water activity | Hygroscopicity | Solubility |
|---|---|---|---|---|---|---|---|
| Constant | | | | | | | |
| $b_0$ | −487.487 | 291.855 | −122.524 | 37.6605 | 1.13769 | 73.6743 | 109.775 |
| Linear | (p = 0.834) | (p = 0.025)* | (p = 0.000)** | (p = 0.000)** | (p = 0.001)** | (p = 0.000)** | (p = 0.104) |
| $b_1$ | −3.63485 | −2.89013 | 0.270425 | 0.305725 | 0.0199450 | −0.655500 | −1.79443 |
| $b_2$ | 20.2741 | 1.03165* | 2.04965 | −1.12255** | −0.0548950** | 0.117500 | 3.08920 |
| $b_3$ | 8.21026 | −5.61250 | 6.46293** | −0.943297* | −0.00493901 | −0.566896** | 0.410703 |
| Square | (p = 0.445) | (p = 0.112) | (p = 0.006)** | (p = 0.496) | (p = 0.364) | (p = 0.002)** | (p = 0.453) |
| $b_{11}$ | 0.0103401 | 0.00940 | −0.00229066 | −0.00103297 | −4.48901 × 10$^{-5}$ | 0.00145604 | 0.00531703 |
| $b_{22}$ | −0.138040 | −0.01160 | −0.0143626 | 0.00646813 | 0.000440440 | −0.00417582 | −0.0201319 |
| $b_{33}$ | 0.0843132 | 0.0615625 | −0.093066** | −0.00114354 | −6.55563 × 10$^{-4}$ | 0.0184753** | 0.000731456 |
| Interactions | (p = 0.634) | (p = 0.201) | (p = 0.152) | (p = 0.234) | (p = 0.290) | (p = 0.015)* | (p = 0.986) |
| $b_{12}$ | 0.0144456 | −0.00160 | 0.00592637 | −5.81319 × 10$^{-4}$ | −1.19396 × 10$^{-4}$ | 0.00325824* | 0.00136868 |
| $b_{13}$ | −0.0493695 | −0.004437 | 0.00240453 | 0.00428915 | 0.000217995 | −0.00344780* | −0.00208585 |
| $b_{23}$ | −0.0391140 | 0.049375 | −0.0371909 | 0.00307830 | −1.01511 × 10$^{-4}$ | 0.00185440 | −2.96703 × 10$^{-4}$ |
| $R^2$ | 0.491 | 0.787 | 0.932 | 0.941 | 0.855 | 0.990 | 0.561 |
| $R^2$ (adj) | 0.000 | 0.573 | 0.864 | 0.883 | 0.710 | 0.980 | 0.121 |
| P (regression) | 0.521 | 0.0033* | 0.000** | 0.000** | 0.007** | 0.000** | 0.361 |

Note:
Subscripts: 1 = inlet air temperature; 2 = outlet air temperature; 3 = maltodextrin percentage
*Significant at 0.05 level.
**Significant at 0.01 level c) Statistical Design and Analysis Response surface methodology was applied for designing of the experiments, analysis of the relationships between variables, and investigating the optimum conditions for spray drying of the dragon fruit juice. The experiments were based on a central composite design, two levels factorial; full factorial, with three independent variables, and 20 runs analyzed at p<0.05. The software used was Minitab V14 Sub100. All analyses were done in triplicates.

d) Betalain Content

Figure 2:
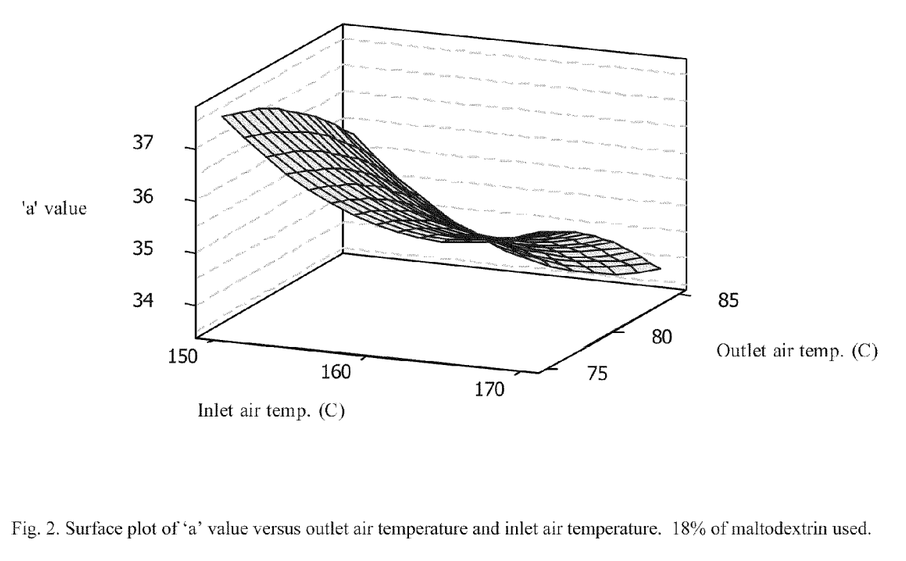
FIG. 2 shows a surface plot of 'a' value versus outlet air temperature and inlet air temperature.

Total betalain content was measured by spectrophotometric analysis in accordance to Herbach et al. (2006) and Moβ-hammer et al. (2005). Dragon fruit powder was dissolved in pH 6.5 McIlvaine buffer and filtered through Whatman No. 1 filter paper. The absorption of the solution should be 0.5-1 at 538 nm when measured using a Lambda 25 UV/VIS spectrometer (Perkin Elmer, Shelton, USA). Solutions with higher absorption values should be diluted accordingly with the buffer. Betalain content (BLC) was calculated by: [BLC (mg/L)=(A×DF×MW×1000)/($\epsilon$×1)], where A is the absorption value at 538 nm corrected by the absorption at 600 nm, DF is the dilution factor and 1 the path length (1 cm) of light e) Colour Measurement Colour was measured with a Hunter Lab Colorimeter (Hunter Lab Associates Laboratory, Virginia, USA). The illuminant used was $D_{25}$ and a standard white plate (No. C222951), having reflectance values of X=81.17, Y=83.27, Z=97.59, was used as a reference. Dragon fruit powder was uniformly packed in a 5 cm×5 cm glass optical cell with 1 cm light path length and the cell was placed at the reflectance port of the colorimeter. Reflected visible light with specular reflection included was measured and results were reported as average of triplicate determinations, as L (lightness), ±a (+a is red and −a is green), ±b (+b is yellow, −b is blue), h° (hue angle) where h°=tan$^{-1}$ (b/a), and C (chroma or saturation) where C=(a$^2$+b$^2$)$^{1/2}$. The colour of the dragon fruit powder produced in terms of its hue, chroma, and lightness is shown in Table 2. There was significant relationship between the independent variables studied and colour (a) and lightness (L) and no significant relationship between independent variables and other colour properties. As the maltodextrin percentage increased, L increased because of the dilution of the colour. FIG. 2 shows that by increasing the temperature, 'a' value or reddish colour decreased.

f) Moisture Content

The moisture content of dragon fruit powder was determined by drying 3 g of powder to constant weight in an air oven at 103° C. as described by Loksuwan (2007). Constant weight was achieved after 4 hr of drying. The best suitable regression equation relating the independent variables and moisture content can be illustrated as in Eq. 1.

$$Y=14.4-0.12X2-0.058X3, R^2=0.868, R^2(adj)=0.851 \quad \text{Eq. 1:}$$

Figure 3:
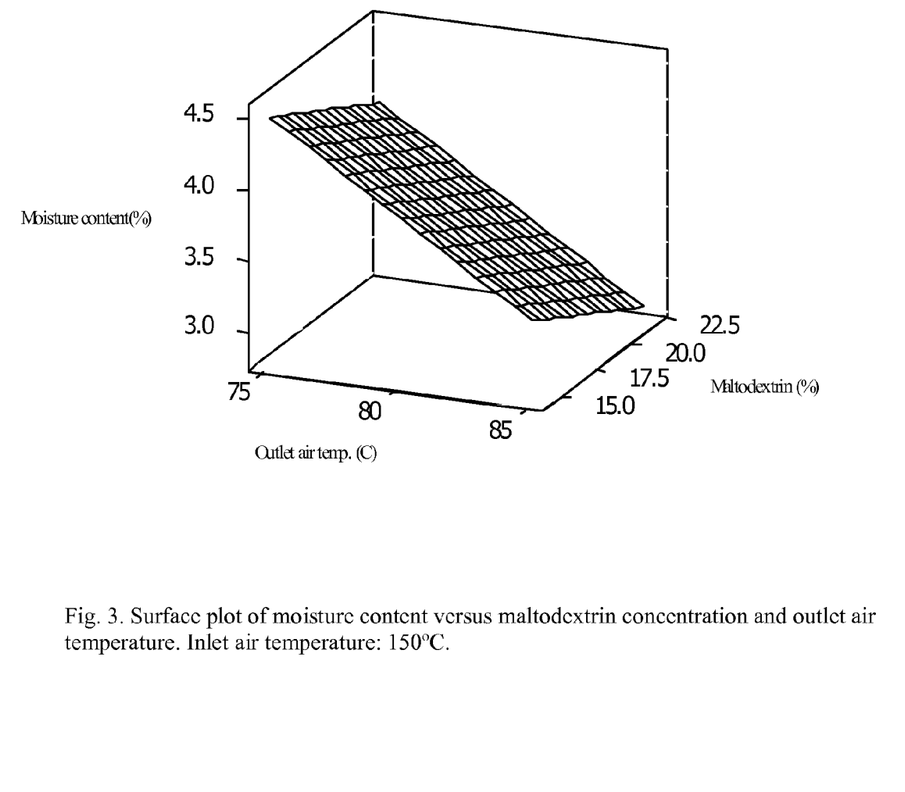
FIG. 3 shows a surface plot of moisture content versus maltodextrin concentration and outlet air temperature.

The regression analysis showed that the regression model fitted the data at $p<0.05$ and there was a negative and very high correlation between X2 and X3 with moisture content (FIG. 3).

The main factor that decreased the moisture content of the dragon fruit powder is the outlet air temperature because the temperature of particles at the end of chamber determines the moisture content of the particles.

Table 3 shows that with an increase in the maltodextrin percentage, the moisture content decreased. This was due to the effect of water content of the feed on the final moisture of the powder. Lower water content of the feed would require lower amount of heat for evaporation.

g) Water Activity

Measurement of water activity was carried out using a water activity meter (AQUALAB Series 3 TE, USA). Water activity ($a_w$) is the ratio of vapour pressure of water in a food system to vapour pressure of pure water at the same temperature. Water activity is a better indicator of shelf life than moisture content and it reflects the availability of free water in a food system that can contribute to biochemical reactions and is responsible for microbiological spoilage.

Figure 4:
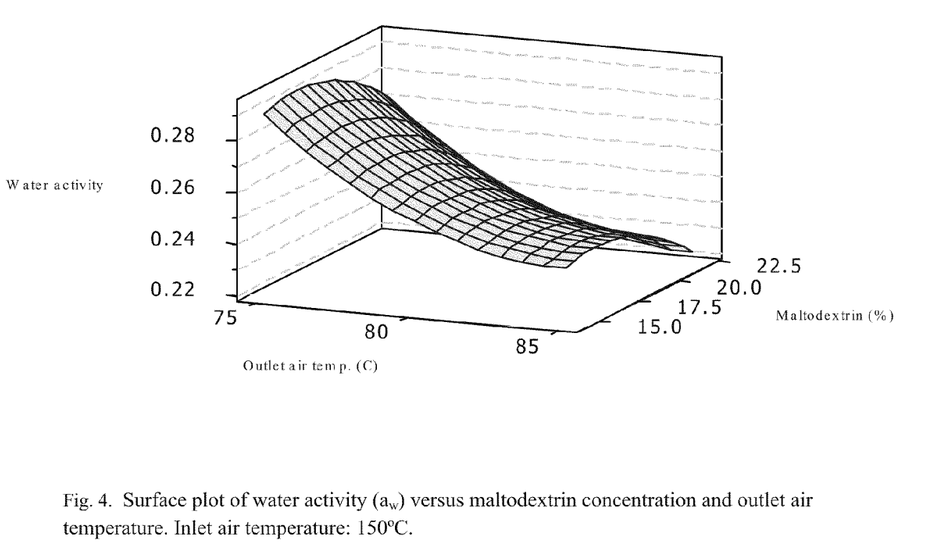
FIG. 4 shows a surface plot of water activity ($a_w$) versus maltodextrin concentration and outlet air temperature.

Although the definition of water activity is separate from that of moisture content but the same observation as moisture content was obtained whereby the outlet air temperature and maltodextrin percentage had significant contributions towards the water activity (FIG. 4), and with an increase in the maltodextrin and outlet air temperature, the water activity was decreased. Table 3 shows water activities of the powders were between 0.213-0.296 and this indicated that the powders produced were relatively stable against biochemical and microbiological activities

TABLE 2

Run order of experiments, betalain retention and color measurement of dragon fruit powders

| Run order | Inlet air temp. (° C.), X1 (x1) | Outlet air temp. (° C.), X2 (x2) | MD DE8-12 (%), X3 (x3) | Betalain retention (%)* | Color* a | b | L | C | h° |
|---|---|---|---|---|---|---|---|---|---|
| 1 | 170(1) | 75(−1) | 22(1) | 94.29 | +34.97 | −18.34 | 50.82 | 39.64 | −27.71 |
| 2 | 160(1) | 80(0) | 18(0) | 97.83 | +35.43 | −20.09 | 49.70 | 40.45 | −29.75 |
| 3 | 160(0) | 85(1) | 18(0) | 92.21 | +34.26 | −17.54 | 48.90 | 38.51 | −27.06 |
| 4 | 160(0) | 80(0) | 18(0) | 94.97 | +34.45 | −18.28 | 49.92 | 39.01 | −27.98 |
| 5 | 150(−1) | 75(−1) | 22(1) | 99.75 | +36.78 | −20.94 | 49.98 | 42.06 | −29.68 |
| 6 | 170(1) | 80(0) | 18(0) | 97.40 | +35.74 | −20.36 | 49.59 | 40.71 | −29.82 |
| 7 | 150(−1) | 85(1) | 22(1) | 95.94 | +37.28 | −18.91 | 48.43 | 42.23 | −26.82 |
| 8 | 160(0) | 80(0) | 18(0) | 99.69 | +36.61 | −21.54 | 49.12 | 42.47 | −30.39 |
| 9 | 160(0) | 80(0) | 22(1) | 98.21 | +36.15 | −19.38 | 49.09 | 41.66 | −28.71 |
| 10 | 150(−1) | 75(−1) | 14(−1) | 92.93 | +39.8 | −23.04 | 44.30 | 46.05 | −30.29 |
| 11 | 160(0) | 75(−1) | 18(0) | 95.20 | +36.72 | −20.45 | 48.85 | 42.26 | −29.23 |
| 12 | 160(0) | 80(0) | 18(0) | 93.81 | +33.73 | −16.95 | 50.63 | 37.54 | −26.87 |
| 13 | 150(−1) | 85(1) | 14(−1) | 90.22 | +36.06 | −18.59 | 45.40 | 41.58 | −27.48 |
| 14 | 150(−1) | 80(0) | 18(0) | 98.98 | +37.70 | −21.86 | 48.42 | 45.20 | −30.13 |
| 15 | 160(0) | 80(0) | 18(0) | 89.63 | +34.35 | −17.27 | 48.87 | 38.49 | −26.89 |
| 16** | 170(1) | 85(1) | 14(−1) | — | — | — | — | — | — |
| 17 | 170(1) | 85(1) | 22(1) | 91.34 | +34.86 | −16.93 | 50.13 | 39.39 | −25.79 |
| 18 | 160(1) | 80(0) | 14(−1) | 98.80 | +37.38 | −21.74 | 46.40 | 43.87 | −30.50 |
| 19 | 160(0) | 80(0) | 18(0) | 91.66 | +33.59 | −17.14 | 50.44 | 37.94 | −27.11 |
| 20 | 170(1) | 75(−1) | 14(−1) | 93.34 | +38.41 | −21.08 | 44.43 | 43.83 | −29.02 |

MD: Maltodextrin
*Data are means of triplicate determinations
**powder was not produced due to the high stickiness of the feed

TABLE 3

Run order of experiments and physical properties of dragon fruit powders

| Run order | Inlet air temp. (° C.), X1 (x1) | Outlet air temp. (° C.), X2 (x2) | MD DE 8-12 (%), X3 (x3) | MC (%)* | Water activity* | Hygro-scopicity (%)* | Solubility (%)* |
|---|---|---|---|---|---|---|---|
| 1 | 170(1) | 75(−1) | 22(1) | 4.27 | 0.285 | 17.8 | 95.50 |
| 2 | 160(0) | 80(0) | 18(0) | 3.75 | 0.263 | 18.9 | 95.64 |
| 3 | 160(0) | 85(1) | 18(0) | 3.30 | 0.248 | 18.9 | 95.97 |
| 4 | 160(0) | 80(0) | 18(0) | 3.69 | 0.250 | 19.0 | 95.49 |
| 5 | 150(−1) | 75(−1) | 22(1) | 3.86 | 0.262 | 18.2 | 96.02 |
| 6 | 170(1) | 80(0) | 18(0) | 3.78 | 0.263 | 19.2 | 95.40 |
| 7 | 150(−1) | 85(1) | 22(1) | 2.71 | 0.213 | 18.0 | 96.40 |
| 8 | 160(0) | 80(0) | 18(0) | 3.64 | 0.253 | 18.8 | 96.52 |
| 9 | 160(0) | 80(0) | 22(1) | 3.75 | 0.258 | 18.1 | 96.16 |
| 10 | 150(−1) | 75(−1) | 14(−1) | 4.82 | 0.296 | 20.4 | 94.90 |
| 11 | 160(0) | 75(−1) | 18(0) | 4.45 | 0.294 | 19.0 | 94.95 |
| 12 | 160(0) | 80(0) | 18(0) | 3.70 | 0.255 | 18.9 | 95.31 |
| 13 | 150(−1) | 85(1) | 14(−1) | 3.53 | 0.258 | 20.1 | 95.78 |
| 14 | 150(−1) | 80(0) | 18(0) | 3.44 | 0.248 | 19.2 | 97.59 |
| 15 | 160(0) | 80(0) | 18(0) | 3.92 | 0.277 | 18.9 | 95.42 |
| 16** | 170(1) | 85(1) | 14(−1) | — | — | — | — |

TABLE 3-continued

Run order of experiments and physical properties of dragon fruit powders

| Run order | Inlet air temp. (° C.), X1 (xl) | Outlet air temp. (° C.), X2 (x2) | MD DE 8-12 (%), X3 (x3) | MC (%)* | Water activity* | Hygro-scop-icity (%)* | Solu-bil-ity (%)* |
|---|---|---|---|---|---|---|---|
| 17 | 170(1) | 85(1) | 22(1) | 3.11 | 0.215 | 18.3 | 96.63 |
| 18 | 160(0) | 80(0) | 14(−1) | 3.64 | 0.241 | 20.6 | 95.79 |

MD: Maltodextrin
*Data are means of triplicate determinations
**powder was not produced due to the high stickiness of the feed h) Hygroscopicity At least 2 g of powder was placed in a dessicator containing saturated ammonium chloride solution with relative humidity of 79.5%. After one week, the moisture gained by the powder was measured and hygroscopic moisture was calculated with the following formula to determine hygroscopicity: [% Hygroscopicity=(% WI+% MC)×100/(100+% WI)] where MC=moisture content of the powder, and % WI=(weight of sample after equilibrium−weight of sample)/weight of sample×100.

Figure 5:
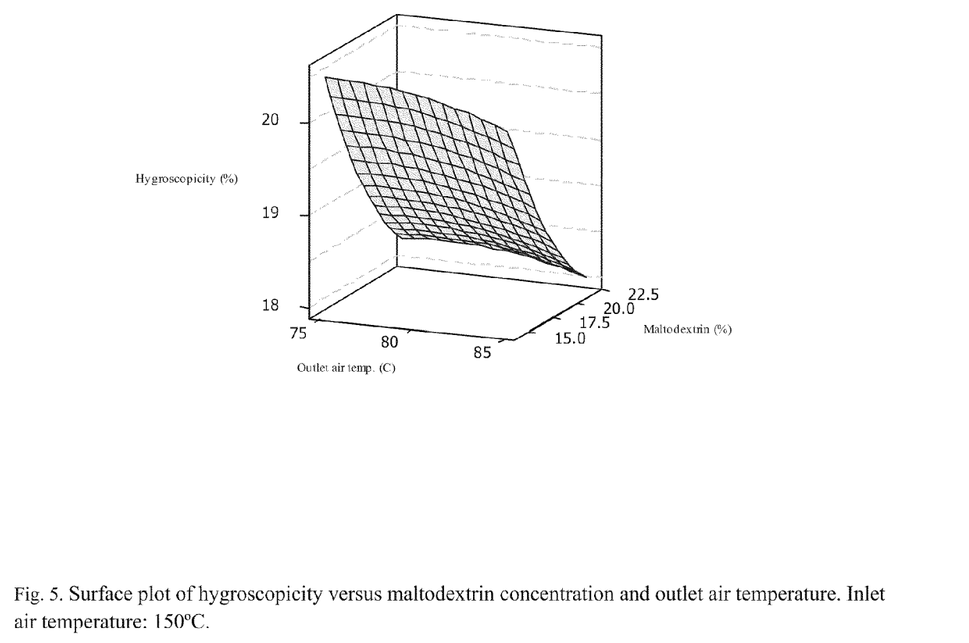
FIG. 5 shows a surface plot of hygroscopicity versus maltodextrin concentration and outlet air temperature.

There were significant correlations between independent variables and hygroscopicity. FIG. 5 shows that maltodextrin percentage has the highest effect on hygroscopicity and with increasing maltodextrin, hygroscopicity decreased.

i) Solubility

Solubility was determined as recommended by Cano-Chauca et al. (2005). 100 ml of water and 1 g of dragon fruit powder were homogenized in a blender for 5 minutes. The solution was then centrifuged (Heraeus Multifuge 3L, Thermo, Germany) at 3000×g for 5 min. An aliquot of 25 ml of the supernatant was transferred to a Petri dish and dried in an oven at 90° C. for 10 hr. The solubility (%) was calculated based on the dry weight of the supernatant compared to its expected dry matter. Table 3 shows that the solubility of the powders was between 94.9-97.6% which are acceptable. In this study, there was no solubility problem as the additive, maltodextrin, has good solubility properties and the composition of fruit was also of highly soluble compounds.

The invention claimed is:

1. A method for manufacturing a natural colorant obtained from *Hylocereus polyrhizus* (red dragon fruit) comprising the steps of:
   a) obtaining red dragon fruit;
   b) removing skin and seeds from said fruit;
   c) obtaining a liquid juice solution from the skinned and de-seeded fruit;
   d) adding maltodextrin at a concentration greater than 20% but not more than 30% (w/w) to said liquid juice solution;
   e) mixing the maltodextrin and liquid juice solution to form a homogenized mixture;
   f) spraying said mixture through a spray drier having a working inlet air temperature between 130° C. and up to but not including 165° C.; and
   g) obtaining a spray-dried powder containing the natural colorant from step f).

2. The method of claim 1, wherein the natural colorant is a bioactive ingredient, wherein the natural colorant includes betalains.

3. The method of claim 1, wherein said natural colorant is a betalain.

* * * * *